United States Patent [19]

Baizer et al.

[11] 4,351,951
[45] Sep. 28, 1982

[54] PROCESS FOR MAKING GLYOXYLATE HEMIACETALS

[75] Inventors: Manuel M. Baizer, Santa Monica, Calif.; Richard D. Goodin, St. Louis, Mo.

[73] Assignee: Monsanto Company, St. Louis, Mo.

[21] Appl. No.: 184,868

[22] Filed: Sep. 8, 1980

Related U.S. Application Data

[63] Continuation-in-part of Ser. No. 972,170, Dec. 21, 1978.

[51] Int. Cl.³ ............................................. C07C 67/36
[52] U.S. Cl. ..................................................... 560/186
[58] Field of Search ............... 560/187, 179, 186, 175, 560/177, 174; 562/587, 519

[56] References Cited

U.S. PATENT DOCUMENTS

| | | | |
|---|---|---|---|
| 1,994,433 | 3/1935 | Olson et al. | 562/519 |
| 3,948,986 | 4/1976 | Suzuki | 560/187 |
| 4,224,420 | 9/1980 | Papanu et al. | 525/401 |

FOREIGN PATENT DOCUMENTS

| | | | |
|---|---|---|---|
| 271589 | 6/1927 | United Kingdom | 562/519 |
| 568512 | 3/1945 | United Kingdom | 560/177 |
| 793807 | 4/1958 | United Kingdom | |
| 797604 | 7/1958 | United Kingdom | |
| 1047408 | 6/1965 | United Kingdom | 560/232 |

OTHER PUBLICATIONS

Gokel, George W. et al., *Aldrichimica Acta*, vol. 9, (1976) pp. 3–12.
Kirk-Othmer, *Encyclopedia of Chemical Technology*, 2nd Ed., (1963) Interscience, Publ. vol. I, pp. 107–109.
Pedersen, C. J., *J. Am. Chem. Society*, vol. 89, (1967) pp. 7017 and 7024.
Bredereck et al., *Angew. Chem.*, vol. 77, (1965) p. 964.

*Primary Examiner*—Natalie Trousof
*Assistant Examiner*—L. Hendriksen

[57] ABSTRACT

The invention relates to the process for making glyoxylate hemiacetals comprising reacting an alcohol of the formula ROH where R is alkyl, or reacting a formate ester of the formula

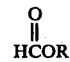

where R is alkyl, with CO under pressure in the presence of a basic initiator of the formula $M^+(OR)^-$ where M is an alkali metal and R is alkyl, and in the presence of a complexing agent for $M^+$ having O and/or N donor atoms capable of solvating $M^+$ or in the presence of a basic initiator of the formula $NR''_4{}^+(OR)^-$ where each R'' is the same or a different alkyl or aralkyl and R is alkyl.

12 Claims, No Drawings

PROCESS FOR MAKING GLYOXYLATE HEMIACETALS

This application is a continuation-in-part of application Ser. No. 972,170, filed Dec. 21, 1978.

BACKGROUND OF THE INVENTION

1. Field of the Invention

A process is described for making glyoxylate hemiacetals from carbon monoxide under pressure with an alcohol or a formate ester. Since methods for converting glyoxylate hemiacetals to the free glyoxylates are known to those skilled in the art, this invention also relates in principle to a novel method for preparing glyoxylates.

2. Description of the Prior Art

There is much literature on the synthesis of glyoxylic acid, its esters and acetals. They have been made from two-carbon atom organic compounds like $C_2H_5OH$, $CH_3COOH$, $Br_2CHCOOH$, $(CHO)_2$, and $HOCH_2COOH$; from three-carbon compounds like glycerine; from four-carbon compounds like $$\begin{array}{c} CHCOOH \\ \parallel \\ CHCOOH \end{array}$$

and tartaric acid.

The literature on the preparation of formate esters from alkali metal alkoxides and CO is also extensive; however, no formation of glyoxylate is reported, and an experiment done by us under similar conditions yielded no glyoxylate.

Formate ester has been deprotonated presumably to $(COOR)^-$ [G. K. Koch et al., Tetrahedron Letters, (7), 603, 1974]; and, the formation of any glyoxylate is not reported and was not observed by us under analogous conditions. Likewise, J. C. Powers et al., Tetrahedron Letters, (22) 1713 (1965) observed deprotonation of HCOOR but failed to obtain reactions of $(COOR)^-$ with electrophiles.

SUMMARY OF THE INVENTION

The invention relates to the process for making glyoxylate hemiacetals comprising reacting an alcohol of the formula ROH where R is alkyl or reacting a formate ester of the formula $$\begin{array}{c} O \\ \parallel \\ HCOR \end{array}$$

where R is alkyl with CO under pressure in the presence of a basic initiator of the formula $M^+(OR)^-$ where M is alkali metal and R is alkyl, and in the presence of a complexing agent for $M^+$ having O and/or N donor atoms capable of solvating $M^+$ or in the presence of a basic initiator of the formula $NR''_4(OR)^-$ where each R'' is the same or a different alkyl or aralkyl and R is alkyl.

DESCRIPTION OF THE PREFERRED EMBODIMENTS

While we do not wish to be bound by any mechanism explaining the synthesis of glyoxylate hemiacetal from formate, we may offer the following equations as hypotheses:

$$CO[OR^-] + ROH \rightleftharpoons HCOOR + [OR^-] \quad [1]$$

$$HCOOR + B^- \rightleftharpoons [COOR]^- + BH \quad [2]$$

$$[COOR]^- \rightleftharpoons CO + OR^- \quad [3]$$

$$[COOR]^- + HCOOR \rightleftharpoons H\overset{O^-}{\underset{OR}{C}}COOR \quad [4]$$

Equation [1] summarizes the formation of formate esters from alcohols and CO using an alkoxide catalyst. In [2] $B^-$ represents a base strong enough to deprotonate the formic ester as shown. These "suitable basic initiators" may be a metal alkoxide in the presence of agents capable of solvating the cation, as, for example, crown ethers, polyamines such as hexamethylenepentamine or tetramethylethylenediamine, or pentaglyme for alkali metal cations, or may be a quaternary ammonium alkoxide. The $B^-$ may also be a carbanion $R'^-$ derived chemically or electrochemically from a carbon acid $R'H$ of high enough $pK_a$ so that $R'^-$ is able to achieve the deprotonation depicted in equation [2]. Again, the counterion for $R'^-$ is chosen from the group given above; the structure of $R'^-$ is such as to minimize nucleophilic attack upon, e.g., esters.

Since the equilibrium depicted in equation [3] liberates $OR^-$ and the latter in conjunction with the proper cation is effective in deprotonating HCOOR according to equation [2], $B^-$ when different from $OR^-$ is a "suitable basic initiator" while $OR^-$ is the effective base.

Glyoxylates are made from hemiacetals by thermal cracking and fractional distillation.

Glyoxylates of the hemiacetals thereof are useful as synthetic intermediates to introduce an aldehyde moiety into certain organic compounds, e.g., in the synthesis of the commercial products vanillin and Ethavan ® by the Riedel-de Haen process. Polymerization of glyoxylate esters followed by stabilization and hydrolysis produces a detergent additive useful as a phosphate replacement.

EXAMPLE 1

1.0 g. (0.0435 mole) of sodium was dissolved in a few milliliters of methanol and excess methanol was removed under vacuum. Then 20 to 30 ml. of tetrahydrofuran was distilled from lithium aluminum hydride onto the dry sodium methoxide to form a slurry. This slurry was placed in an autoclave at 25° C. and pressured to 1300 p.s.i. with carbon monoxide. A mixture of 60 ml. (58.4 g. and 0.974 mole) of methyl formate and 1.2 ml. of 15-crown-5 ether was added to the autoclave. The autoclave was then pressured to 3000 p.s.i. and allowed to run (agitate) at 25° C. for 19 hours. Pressure had dropped to 1300 p.s.i. and 2.5 ml. (2.61 g. and 0.0435 mole) of glacial acetic acid in tetrahydrofuran was added under pressure to quench the reaction.

The reaction mixture was almost jelly-like in consistency. A gas chromatographic analysis showed approximately equal amounts of methanol and methyl glyoxylate as well as methyl formate, tetrahydrofuran and acetic acid. It should be noted that gas chromatography, the primary analytical method used in these studies, does not differentiate between methyl glyoxylate and methyl glyoxylate methylhemiacetal due to the thermal elimination of methanol from the hemiacetal producing methyl glyoxylate during analysis. Thus, injection of an authentic sample of hemiacetal onto a gas chromatography column gives peaks corresponding to methanol and methyl glyoxylate.

To define the form of the glyoxylate present in the reaction mixture, the solids were removed by filtration to give a light yellow filtrate. The solids were water-soluble, and nuclear magnetic resonance (nmr) analysis indicated predominantly sodium acetate, the expected product of neutralization, and a small amount of sodium formate.

The volatile components of the filtrate were removed under slightly reduced pressure to give a golden oily residue. Nuclear magnetic resonance analysis confirmed methyl glyoxylate methylhemiacetal, identical to the spectrum of an authentic sample. Gas chromatographic analysis of the residue again showed methanol and methyl glyoxylate peaks.

The presence of methyl glyoxylate hemiacetal was further confirmed by preparing the known derivatives: 2,4-dinitrophenylhydrazone, m.p. 198°–200° C. [lit. m.p. 200.5°–201° C., A. Ross and R. N. Ring, *J. Org. Chem.*, 26, 579(1961)]; semicarbazone, m.p. 225°–26° C. (d) [lit. 226° C. (d), V. Uchytilova and J. Gut., *Coll. Czech. Chem. Commun.*, 36, 2383 (1971)]; phenylhydrazone, m.p. 138°–39° C. [lit. 139° C., C. Harries, *Chem. Ber.*, 36, 1936 (1903)]. The preparation of the derivatives confirms only the presence of the methyl glyoxylate moiety and does not differentiate between methyl glyoxylate and methyl glyoxylate methylhemiacetal.

These data indicate that the product of the reaction is methyl glyoxylate methylhemiacetal which undoubtedly exists before quenching as the sodium salt as shown in equation [4]. This salt cannot be further characterized without acid quenching under pressure due to the reversible nature of its formation as indicated in the equation [4] and [3].

EXAMPLE 2

This experiment is essentially a repeat of Example 1, except that 1.5 ml. of the crown ether was used rather than 1.2 ml. Initial pressure (after the formate addition and pressuring) was 3015 p.s.i. After 16.5 hrs., the pressure had dropped to 2950 p.s.i. The reaction mixture was quenched with the acetic acid in tetrahydrofuran. Reaction mixture is white and more fluid than in Example 1. Gas chromatograph shows methyl glyoxylate, but see discussion in Example 1 indicating the gas chromatograph would not show the hemiacetal.

The reaction mixture was diluted with methylene chloride and filtered. Volatiles were removed from the filtrate at ~35° C. under reduced pressure (water aspirator) to give a slightly yellow oily liquid residue. Nuclear magnetic resonance analysis gave a spectrum fitting that of the methyl hemiacetal or methyl glyoxylate.

EXAMPLE 3

This experiment begins with methanol instead of methyl formate. 2.3 g. (0.1 mole) of sodium was dissolved in 80 ml. (63.2 g. and 1.98 mole) of methyl alcohol under nitrogen blanketing to give a slightly turbid solution. Addition of 2.0 ml. of the 15-crown-5 ether cleared the solution somewhat. This reaction mixture was charged to the autoclave under argon purge, and the autoclave was pressured to 3000 p.s.i. with CO. Pressure dropped at a progressively faster rate resulting in a sharp exotherm and pressure drop to a maximum temperature to 56° C. in 75 min. Pressure then leveled off and dropped slowly through the remainder of the run. During the initial part of the run, the autoclave was periodically repressured to 3800 p.s.i. Total pressure drop during the first 2 hours of the run was 2400 p.s.i. and only 265 p.s.i. during the next 16 hours. At the end of the run, pressure had dropped to 1300 p.s.i. and the reaction mixture was quenched with 6 ml. (0.105 mole) of glacial acetic acid in methanol. The reaction mixture was an off-white frothy slurry.

Gas chromatography showed the presence of methyl glyoxylate, methyl formate, methanol and an unidentified peak. Nuclear magnetic resonance tests were not run on the sample because of more extensive sample preparation required, so the proof of the existence of the hemiacetal was not possible. See discussion in Example 1.

Although methanol instead of methyl formate was used as starting material in this example, the actual reactant is undoubtedly methyl formate formed in situ in the early stages of the reaction as outlined in equation [1]. This process is well known and forms the basis for the commercial production of methyl formate. Initial formation of methyl formate is demonstrated by the exotherm and rapid uptake of CO and by the gas chromatographic analysis. There is no reason to believe that the chemistry of the methanol experiment differs in any way from that of the methyl formate experiments.

EXAMPLE 4

Instead of the 15-crown-5 ether in this experiment tetramethylenediamine (TMEDA) is used as the complexing agent. 2.3 (0.1 mole) of sodium was dissolved in 80 ml. (63.2 g. and 1.98 mole) of methanol and 15.1 ml. (11.6 g. and 0.1 mole) of TMEDA was added. The reaction mixture was charged into a dry autoclave and pressured to 3000 p.s.i. with CO. Uptake of CO became progressively faster with a sharp uptake and accompanying exotherm (34° C. maximum) up to 95 minutes. Pressure then leveled off and additional uptake over the next 19 hours was slow. Pressure uptake of CO was 2595 p.s.i. for the first 2 hours of the run and 220 p.s.i. during the next 19 hours. Pressure was decreased to 1300 p.s.i. and the reaction mixture was quenched with 6 ml. (0.105 mole) of glacial acetic acid in methanol. The reaction mixture was an off-white frothy slurry.

Gas chromatography analysis shows the presence of methyl glyoxylate, methyl formate, methanol and a small amount of unidentified material observed previously with the crown ether. Nuclear magnetic resonance tests were not run to prove the presence of the hemiacetal. See discussion in Example 1.

The complexing agents used for the $M^+$ of the $M^+OR^-$, suitable basic initiators, are in general, compounds with donor atoms (O,N) known to solvate $M^+$, and these complexing agents may be acyclic or heterocyclic. One crown ether has been used in examples and many are known or available from which to choose other suitable ethers, e.g. the article "Crown Ether Chemistry; Principles and Applications", by George W. Gokel and H. du Pont Durst, Aldrichimica Acta, 9, pp 3–12 (1976) which is incorporated herein by reference. Another complexing agent is illustrated in Example 4, namely tetramethylenediamine and many other polyamines of this type are well-known and commercially available. Other basic initiators suitable for carrying out the process of this invention which require no added complexing agents are compounds of the formula $NR''_4{}^+(OR)^-$ where each $R''$ is the same or a different alkyl or aralkyl with the preferred number of carbon atoms in each group being not more than 10.

The basic initiators are of the formula $M^+(OR)^-$ where M is an alkali metal and R is alkyl in combination with a suitable complexing agent described in the previous paragraph, or compounds of the type, $NR''_4{}^+(OR)^-$. In the examples M is sodium and R is methyl; however, the other alkali metals are operable in the process of the invention, namely lithium, potassium, rubidium and cesium, and R can be any alkyl group, preferably not more than about 10 carbon atoms but normally alkyl groups of not more than 4 carbon atoms are used, e.g. ethyl, n-propyl, isopropyl, n-butyl, isobutyl, t-butyl and the like. Likewise, the $R''$ is normally an alkyl group of not more than 4 carbon atoms but can have 10 or more carbon atoms or an aralkyl group of not more than about 10 carbon atoms. Solid insoluble ionic initiators can also be used, e.g., ion exchange resins.

The temperature, pressure, concentration of initiator and amount of complexing agent chosen for the practice of this invention are chosen on the basis of the rate described, the cooling/heating, pressure and capacity available for operation in relatively inexpensive equipment. It is obvious that the process is operable under a range of conditions on either side of those already used and which in fact have been used in reactions not including the complexing agent but the other ingredients, and thus these previously used conditions and amounts of reactants are not unique, narrowly critical or even optimum.

The isolation of the product may follow the examples given or may be carried out by suitable fractional distillation procedures known in the art.

Inert solvents can be included and tetrahydrofuran has been used in the examples; however, the reaction is operable in the absence of an inert solvent and other inert solvents or reaction mediums can be used.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is clamed is:

1. A process for making glyoxylate hemiacetals comprising reacting an alcohol of the formula ROH where R is alkyl or reacting formate ester of the formula

where R is alkyl with CO under pressure in the presence of a basic iniator of the formula $M^+(OR)^-$ where M is an alkali metal and R is alkyl, and in the presence of a complexing agent for $M^+$ selected from ethers and polyamines and having O and/or N donor atoms capable of solvating $M^+$, or in the presence of a basic initiator of the formula $NR''_4{}^+(OR)^-$ where each $R''$ is the same or a different alkyl or aralkyl and R is alkyl.

2. A process of claim 1 wherein an inert solvent is present.

3. A process of claim 2 wherein said inert solvent is tetrahydrofuran.

4. A process of claim 1 wherein said alkali metal is sodium.

5. A process of claim 1 wherein said $M^+(OR)^-$ is sodium methoxide.

6. A process of claim 1 wherein said formate ester is methyl formate.

7. A process of claim 1 wherein said complexing agent is 15-crown-5 ether.

8. A process of claim 1 wherein said alcohol is methanol.

9. A process of claim 1 wherein said complexing agent is tetramethylethylenediamine.

10. A process of claim 1 wherein said alcohol is methanol, said initiator is sodium methoxide, said complexing agent in 15-crown-5 ether, and said hemiacetal is methyl glyoxylate methylhemiacetal.

11. The process of claim 1 in which the complexing agent is a crown ether.

12. The process of claim 1 in which the complexing agent is a polyamine.

* * * * *